United States Patent
Izumi (10) Patent No.: US 10,145,829 B2
(45) Date of Patent: Dec. 4, 2018

(54) LASER PROCESSING SYSTEM FOR MONITORING IMPURE GAS IN LASER OPTICAL PATH

(71) Applicant: FANUC CORPORATION, Minamitsuru-gun, Yamanashi (JP)

(72) Inventor: Takashi Izumi, Minamitsuru-gun (JP)

(73) Assignee: FANUC CORPORATION, Yamanashi (JP)

( * ) Notice: Subject to any disclaimer, the term of this patent is extended or adjusted under 35 U.S.C. 154(b) by 261 days.

(21) Appl. No.: 15/266,020

(22) Filed: Sep. 15, 2016

(65) Prior Publication Data

US 2017/0082587 A1    Mar. 23, 2017

(30) Foreign Application Priority Data

Sep. 17, 2015  (JP) .................. 2015-184455

(51) Int. Cl.

| | |
|---|---|
| *B23K 26/00* | (2014.01) |
| *G01N 33/00* | (2006.01) |
| *B23K 26/142* | (2014.01) |
| *B23K 26/14* | (2014.01) |
| *B23K 26/70* | (2014.01) |
| *H01S 3/00* | (2006.01) |
| *B23K 26/12* | (2014.01) |

(52) U.S. Cl.
CPC ....... *G01N 33/0036* (2013.01); *B23K 26/128* (2013.01); *B23K 26/142* (2015.10); *B23K 26/1437* (2015.10); *B23K 26/707* (2015.10); *H01S 3/0071* (2013.01)

(58) Field of Classification Search
CPC .... B23K 26/12; B23K 26/128; B23K 26/142; B23K 26/1437; B23K 26/707; G01N 33/0031; G01N 33/0036; H01S 3/0071
See application file for complete search history.

(56) References Cited

U.S. PATENT DOCUMENTS 6,894,248 B2    5/2005   Arakawa et al.

FOREIGN PATENT DOCUMENTS

| JP | H07209152 A | 8/1995 |
|---|---|---|
| JP | 2002357576 A | 12/2002 |
| JP | 4335154 B2 | 9/2009 |
| WO | 2004103633 A1 | 7/2006 |

OTHER PUBLICATIONS

Notification of Reasons for Refusal for Japanese Application No. 2015-184455, dated Sep. 12, 2017, including English translation, 6 pages.

*Primary Examiner* — Dana Ross
*Assistant Examiner* — Brandon Harvey
(74) *Attorney, Agent, or Firm* — RatnerPrestia (57) ABSTRACT

A laser processing system herein includes a laser oscillator, a laser optical path that guides laser beam from the laser oscillator to a workpiece, a purge gas supply line for supplying a purge gas into the laser optical path, oxygen sensor and an impure gas sensor which detects an impure gas influencing the propagation of the laser beam that are installed in the laser optical path, and an impure gas sensor output value correction unit. The impure gas sensor output value correction unit corrects an output value of the impure gas sensor based on an output value of the oxygen sensor.

12 Claims, 8 Drawing Sheets

LASER PROCESSING SYSTEM FOR MONITORING IMPURE GAS IN LASER OPTICAL PATH

BACKGROUND OF THE INVENTION

1. Field of the Invention

The present invention relates to a laser processing system including a laser optical path that guides laser beam emitted from a laser oscillator to an object to be processed.

2. Description of the Related Art

When such impure gases as to diffuse or absorb laser beam is present around a laser processing system, a large influence on a laser beam propagation property is generated. Accordingly, in a conventional laser processing system in which a laser oscillator is mounted, a laser optical path including an optical system that guides the laser beam from a beam emission port of the laser oscillator to a processing point is provided. Moreover, such a laser optical path is filled with a clean purge gas that fails to influence the laser beam propagation property, which allows laser processing to be stable.

Further, Japanese Patent Publication No. 4335154 discloses an invention of the conventional laser processing system as described above, in which a gas sensor for detecting impure gases is provided in the laser optical path to determine whether or not the impure gases were mixed in the laser optical path.

Meanwhile, in the conventional laser processing system as described above, in accordance with improved precision of laser processing and improved output, a purge gas that is to fill the laser optical path is diversified. For example, a dry air, an air in which carbon dioxide causing scattering of laser is reduced, nitrogen-rich gas (i.e., gas containing nitrogen as a main component), nitrogen gas or the like is used as the purge gas.

In particular, a special filter, such as a hollow fiber filter, an oil mist filter, an activated carbon filter or the like is used to generate a dry air or an air in which carbon dioxide is reduced. However, when a gas is allowed to permeate such a special filter, oxygen concentration in the purge gas increases or decreases. Then, the oxygen concentration in the laser optical path greatly changes with passage of time. At this time, even when the impure gases are not mixed in the laser optical path, the gas sensor reacts to a change of the oxygen concentration and an output value of the gas sensor also changes with passage of time. Consequently, when the gas in which the oxygen concentration is changed is used as the purge gas, it will be difficult to correctly determine whether or not the impure gases were mixed in the laser optical path.

In addition, when whether or not the impure gases were mixed in the laser optical path is determined, the output value of the gas sensor is compared with a predetermined determination threshold value. With respect to the determination threshold value, a certain allowance range is commonly set in consideration of an error of the output value of the gas sensor due to an environment. That is the reason why, as the environment in which the laser processing system is installed, such as a temperature, a humidity and an altitude, changes, the output value of the gas sensor relative to the same gas type also slightly changes. However, when the determination threshold value including the certain allowance range is thus set, determination of a mixing of the impure gases may contain an error if the output value of the gas sensor changes in accordance with the change of the oxygen concentration in the laser optical path. Thereby, the laser processing system may erroneously operate.

SUMMARY OF INVENTION

The present invention provides a laser processing system that can highly accurately detect a mixing of impure gases in a laser optical path even when oxygen concentration in the laser optical path changes.

According to the first aspect of the present invention, provided is a laser processing system including:
 a laser oscillator configured to oscillate a laser beam;
 a laser optical path that guides the laser beam from the laser oscillator to an object to be processed;
 an oxygen sensor for detecting oxygen and an impure gas sensor for detecting an impure gas influencing propagation of the laser beam that are installed in the laser optical path; and
 an impure gas sensor output value correction unit that is configured to correct an output value of the impure gas sensor based on an output value of the oxygen sensor.

According to the second aspect of the present invention, provided is the laser processing system according to the first aspect, wherein the impure gas sensor includes at least two impure gas sensors that have different detection concentrations.

According to the third aspect of the present invention, provided is the laser processing system according to the first aspect or the second aspect, wherein the impure gas sensor includes at least two impure gas sensors that detect different gas types.

According to the fourth aspect of the present invention, provided is the laser processing system according to any one of the first aspect to the third aspect, further including:
 an impure gas mixing determination unit that is configured to determine whether or not the impure gas was mixed in the laser optical path, based on a comparison of the output value of the impure gas sensor that is corrected by the impure gas sensor output value correction unit and a determination threshold value that is stored in advance.

According to the fifth aspect of the present invention, provided is the laser processing system according to the fourth aspect, further including:
 a communication device that is configured to communicate a mixing of the impure gas when the impure gas mixing determination unit determines that the impure gas was mixed in the laser optical path.

According to the sixth aspect of the present invention, provided is the laser processing system according to the fourth aspect or the fifth aspect, further including:
 an impure gas adsorbent that adsorbs the impure gas; and
 an exposure function part that is configured to expose the impure gas adsorbent in the laser optical path when the impure gas mixing determination unit determines that the impure gas was mixed in the laser optical path.

According to the seventh aspect of the present invention, provided is the laser processing system according to any of the fourth aspect to the sixth aspect, further including:
 a storage unit that stores the output value of each of the impure gas sensor and the oxygen sensor together with date and hour at which the output value is outputted.

According to the eighth aspect of the present invention, provided is the laser processing system according to any of the first aspect to the seventh aspect, in which
 the laser optical path is provided with a detachable sensor unit, and the sensor unit includes the oxygen sensor and the at least one impure gas sensor.

According to the ninth aspect of the present invention, provided is the laser processing system according to any of the first aspect to the eighth aspect, including:

a purge gas supply line for supplying a purge gas into the laser optical path, in which the purge gas is an air that is supplied into the laser optical path through a high polymer filter, an activated carbon filter, a hollow fiber filter, or an oil mist filter.

According to the tenth aspect of the present invention, provided is the laser processing system according to any of the first aspect to the ninth aspect, in which the oxygen sensor or the impure gas sensor is a controlled potential electrolysis type gas sensor, a galvanic cell type gas sensor, a catalytic combustion type gas sensor, a gas heat conduction type gas sensor, a zirconia type gas sensor, a polaro type gas sensor, or a semiconductor type gas sensor.

BRIEF DESCRIPTION OF THE DRAWINGS

These objects, features, and advantages of the present invention and other objects, features, and advantages will become further apparent from the detailed description of typical embodiments of the present invention that are illustrated in the accompanying drawings.

DETAILED DESCRIPTION

Next, embodiments of the present invention will be described with reference to the drawings. In the following figures, the same components will be assigned the same reference signs. In addition, it is assumed that the elements denoted by the same reference signs in different drawings denotes elements having the same functions. Further, to facilitate understanding, these figures are suitably changed in scale.

First Embodiment

Figure 1:
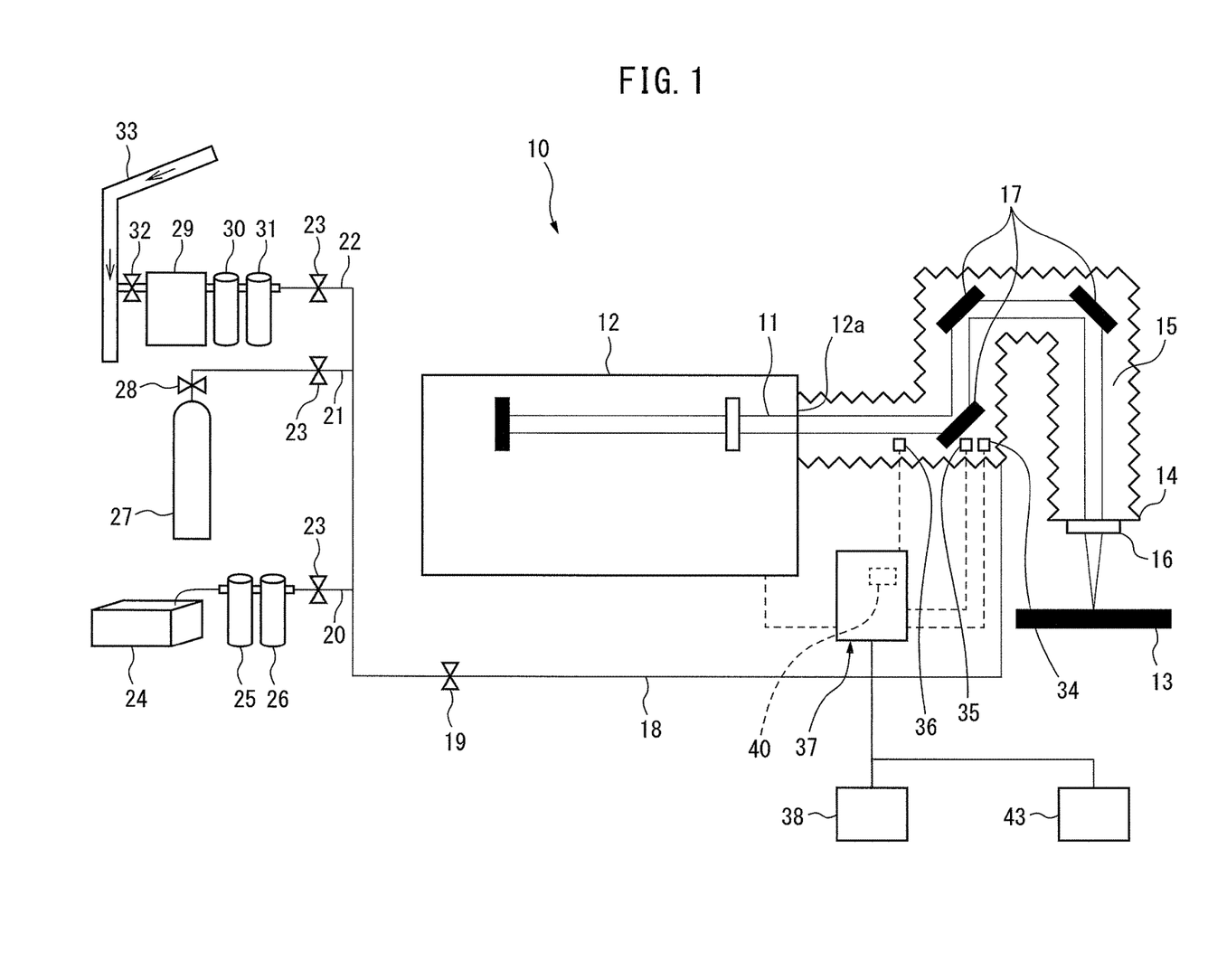
FIG. 1 is a block diagram schematically illustrating a configuration of a laser processing system according to a first embodiment.

FIG. 1 is a block diagram schematically illustrating a configuration of a laser processing system according to a first embodiment.

As illustrated in FIG. 1, a laser processing system 10 according to the first embodiment includes a laser oscillator 12 that oscillates laser beam 11, a processing head unit 14 that radiates the laser beam 11 over a workpiece 13 that is an object to be processed, and a laser optical path 15 that guides the laser beam 11 from a laser beam emission port 12a of the lase oscillator 12 to the workpiece 13 while an optical axis thereof is maintained. Further, the laser processing system 10 includes a numerical value calculator 37 as a control device that controls an operation of the laser oscillator 12 and a movement of the processing head unit 14. Note that the laser oscillator 12 in the present embodiment is a carbonic acid gas laser that processes a metal or a nonmetal using a laser in a factory. However, the laser oscillator applied to the present invention is not limited thereto, but may be another gas laser, or a solid state laser, a semiconductor laser, or the like.

The processing head unit 14 is provided with a condenser lens 16 that collects the laser beam 11 over the workpiece 13. Further, as illustrated in FIG. 1, an optical system, such as mirrors 17 that guide the laser beam 11 emitted from the laser oscillator 12 to the condenser lens 16 of the processing head unit 14 while bending the same in a bending direction of the laser optical path 15, is installed in the laser optical path 15. In addition, the processing head unit 14 is configured to be capable of relatively moving in relation to the workpiece 13 using an unillustrated guide member and drive mechanism. Accordingly, the laser optical path 15 is made of an elastic bellows made of, for example, a rubber or a metal. As a matter of course, the laser optical path 15 is not limited to that made of a bellows. The laser optical path 15 may be that in which, for example, bending portions of the laser optical path 15 are made of a bellows and the other portions are made of a metal pipe.

Further, as illustrated in FIG. 1, to the laser optical path 15, a purge gas supply tube 18 for supplying a purge gas that fails to influence the propagation of the laser beam 11 into the laser optical path 15 is connected. The purge gas supply tube 18 is provided with an opening and closing valve 19. Moreover, the opening and closing valve 19 is operated to close, whereby supplying the purge gas to the laser optical path 15 is configured to be stopped.

In addition, in the laser processing system according to the present embodiment, any of three types of purge gases, such as a dry air, nitrogen gas, and an air in which carbon dioxide is reduced, is configured to be selected and to be capable of being supplied into the laser optical path 15. Accordingly, as illustrated in FIG. 1, to a portion of the purge gas supply tube 18 upstream of the opening and closing valve 19, a supply line 20 of the dry air, a supply line 21 of the nitrogen gas, and a supply line 22 of the air in which carbon dioxide is reduced are each connected. Each of the supply lines 20, 21, 22 is provided with an opening and closing valve 23. Then, one of the three opening and closing valves 23 is opened, and therefore the purge gas supplied into the laser optical path 15 is selected. Note that the "air in which carbon dioxide is reduced" is an air in which concentration of carbon dioxide contained in the air is configured to be a predetermined value or less, for example, 150 ppm or less.

To the supply line 20 of the dry air, a dry pump 24, an activated carbon filter 25, and a high polymer filter 26 are serially connected sequentially along a flow direction of the air. To supply the dry air into the laser optical path 15, only the opening and closing valve 23 of the supply line 20 is opened and the other opening and closing valves 23 of the supply lines 21, 22 are closed. Then, the air is taken in by the dry pump 24 and is allowed to pass sequentially through the activated carbon filter 25 and the high polymer filter 26. Thereby, impurities and organic components in the air are removed while the air is dehumidified. In other words, the dry air is supplied via the purge gas supply tube 18 into the laser optical path 15.

Moreover, to the supply line 21 of the nitrogen gas, nitrogen gas bottle 27 and a flow rate control valve 28 are serially connected sequentially along a flow direction of the nitrogen gas. The flow rate control valve 28 may be an opening and closing valve. To supply the nitrogen gas into the laser optical path 15, only the opening and closing valve 23 of the supply line 21 is opened, the other opening valves 23 of the supply lines 20, 22 are closed, and the flow rate control valve 28 is opened. Thereby, the nitrogen gas that fills the nitrogen gas bottle 27 is supplied via the purge gas supply tube 18 into the laser optical path 15.

In addition, to the supply line 22 of the air in which carbon dioxide is reduced, an oil mist filter 29, an activated carbon filter 30, and a hollow fiber filter 31 are serially connected sequentially along a flow direction of the air. Further, to the oil mist filter 29, a compressed air line 33 of the factory is connected through an opening and closing valve 32. To supply the air in which carbon dioxide is reduced into the laser optical path 15, only the opening and closing valve 23 of the supply line 22 is opened, the other opening valves 23 of the supply lines 20, 21 are closed, and the opening and closing valve 32 is opened. Thereby, the compressed air of the factory is allowed to pass sequentially through the oil mist filter 29, the activated carbon filter 30, and the hollow fiber filter 31. As a result, oil components, impurities and organic components in the compressed air of the factory are removed while carbon dioxide in the air is removed. In other words, the air in which carbon dioxide is reduced, for example, an air in which concentration of carbon dioxide is 150 ppm or less, is supplied via the purge gas supply tube 18 into the laser optical path 15.

Moreover, when a thinner or a paint is used in the vicinity of the laser processing system 10 according to the present embodiment, impure gases containing organic components may be mixed in the laser optical path 15. The impure gases cause absorption and scattering of the laser beam, and, as a result, hinder the propagation of the laser beam and lower a processing ability of a laser processing machine. Accordingly, as illustrated in FIG. 1, in the laser optical path 15, a plurality of types of impure gas sensors 34, 35 detecting the plurality of types of impure gases, respectively, that influence the propagation of the laser beam 11 and oxygen sensor 36 detecting oxygen are installed.

In the present embodiment, the oxygen sensor 36 is a galvanic cell type gas sensor. The impure gas sensors 34, 35 are catalytic combustion type ethanol sensors.

As a matter of course, as the impure gas sensors 34, 35, gas sensors other than the catalytic combustion type gas sensors may be used, and, in the oxygen sensor 36 as well, a gas sensor other than the galvanic cell type gas sensor may be used. In other words, as the gas sensors used as the impure gas sensors 34, 35 and the oxygen sensor 36, any of a controlled potential electrolysis type gas sensor, a galvanic cell type gas sensor, a catalytic combustion type gas sensor, a gas heat conduction type gas sensor, a zirconia type gas sensor, a polaro type gas sensor, a semiconductor type gas sensor, and an electrochemical gas sensor may be suitable.

Further, since the impure gases that influence the propagation of the laser beam 11 include sulfur hexafluoride, ethylene, halogenated hydrocarbon, ammonia, acetone, alcohol, a carbonic acid gas, and the like, the impure gases to be detected are not limited to ethanol. Accordingly, in the present embodiment, in addition to the two impure gas sensors 34, 35 that detect ethanol having different concentrations, at least one gas sensor that detects an impure gas of a gas type different from ethanol may be installed in the laser optical path 15. Alternatively, either of the two impure gas sensors 34, 35 may be a gas sensor that detects an impure gas of a gas type different from ethanol.

Note that, hereinafter, the impure gas sensors 34, 35 will be described as ethanol sensors, based on which the description will be made.

In the present embodiment, concentrations of ethanol that can be detected by the ethanol sensors 34, 35 are preferably different from each other. For example, it is configured that the ethanol sensor 34 on one hand detects an ethanol concentration of 10 to 300 ppm (0.001 to 0.03%), and the ethanol sensor 35 on the other hand detects an ethanol concentration of 200 to 1000 ppm (0.02 to 0.1%).

Further, the ethanol sensors 34, 35 and the oxygen sensor 36 are each electrically connected to the numerical value calculator 37.

The numerical value calculator 37 corrects obtained output values of the ethanol sensors 34, 35 based on an output value of the oxygen sensor 36. Further, the numerical value calculator 37 transmits a corrected output value of each of the ethanol sensors 34, 35 to a display device 38.

Then, the display device 38 is configured to display in a real-time manner the value of each of the ethanol sensors 34, 35 and the oxygen sensor 36 that are transmitted from the numerical value calculator 37. Note that the display device 38 is preferably composed of, for example, a cathode ray tube (CRT), a liquid crystal display, or the like.

Features in which output values of the impure gas sensors, such as the ethanol sensors 34, 35, are corrected will be described in detail.

Figure 2:
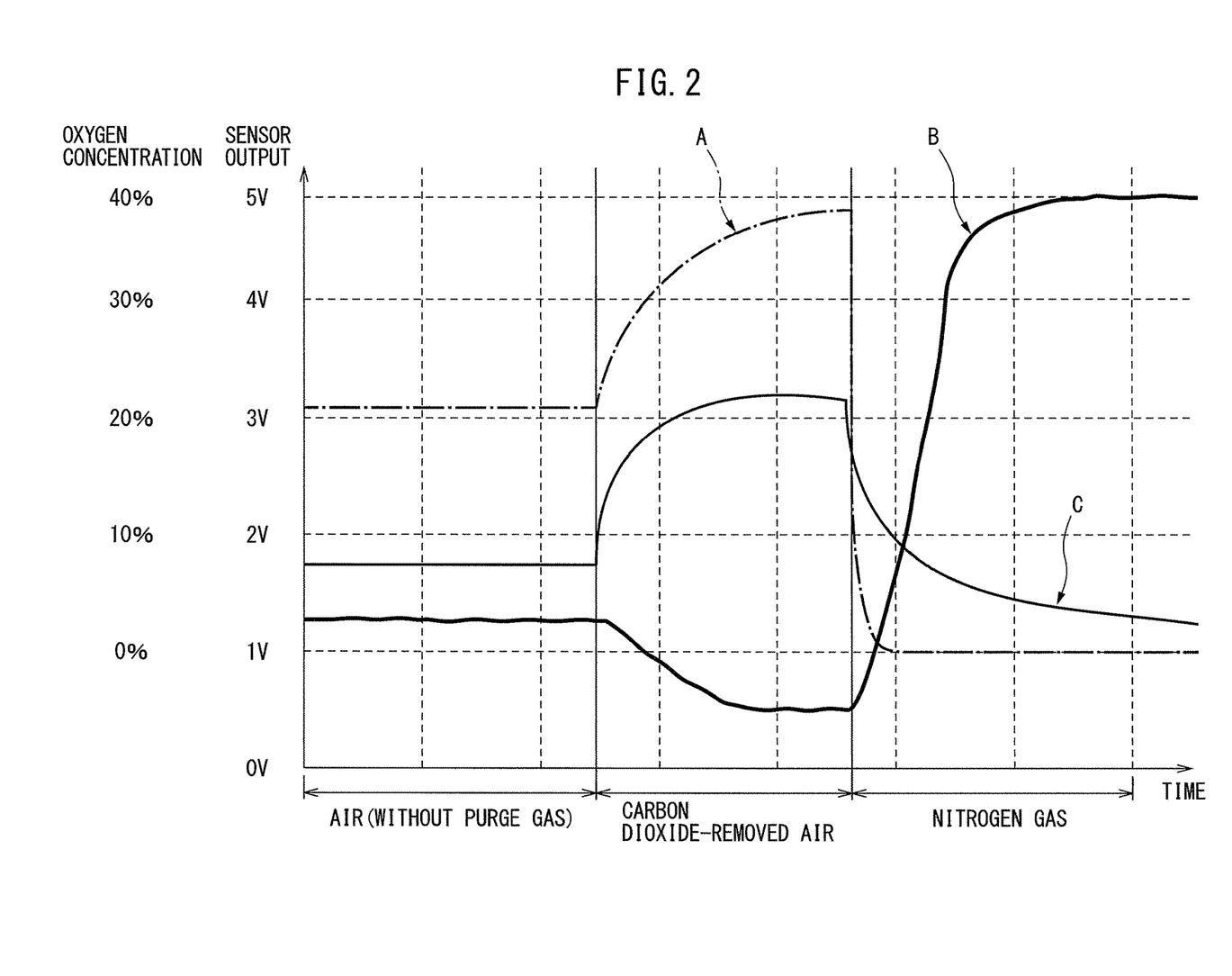
FIG. 2 is a graph illustrating an output value of each of an impure gas sensor, an oxygen sensor, and an ammonia sensor that are installed in a laser optical path as illustrated in FIG. 1 together with passage of time.

FIG. 2 is a graph illustrating an output value of each of the ethanol sensor 35, the oxygen sensor 36, and an ammonia sensor (unillustrated) that are installed in the laser optical path 15 as illustrated in FIG. 1 together with passage of time. In obtaining the graph, the ammonia sensor is installed in place of the ethanol sensor 34 in the laser optical path 15 as illustrated in FIG. 1. Note that in the graph of FIG. 2, a one-dot-chain line A represents an output value of the oxygen sensor 36, a solid line B represents an output value of the ethanol sensor 35, and a solid line C represents an output value of the ammonia sensor.

As illustrated along a horizontal axis of the graph of FIG. 2, a gas environment in the laser optical path 15 as illustrated in FIG. 1 is switched in an order from the air (i.e. an initial state in which the purge gas is not supplied into the laser optical path 15) to the carbon dioxide-removed air (i.e. the air in which carbon dioxide concentration is configured to be a predetermined value or less, for example, 150 ppm or less), and the nitrogen gas. At this time, it is assumed that the impure gases are not mixed in the laser optical path 15. In addition, while the carbon dioxide-removed air is introduced, the air is allowed to pass through a special hollow fiber filter and carbon dioxide is reduced using a difference of permeation rates of the carbon dioxide and the nitrogen gas during passage through the hollow fiber filter. Then, due to a difference of permeation rates of oxygen and the nitrogen gas passing through the hollow fiber filter as described above, oxygen concentration becomes high. In other words, as illustrated in FIG. 2, the output value of the oxygen sensor 36 increases with passage of time. Such an increase of the oxygen concentration may similarly occur also when the air is allowed to pass through a special filter other than the hollow fiber filter, such as a high polymer filter, an activated carbon filter, and an oil mist filter. Moreover, as apparent from FIG. 2, when the oxygen concentration in the laser optical path 15 increases, the output value of each of the ethanol sensor 35 and the ammonia sensor changes. In FIG. 2, the output value of the ethanol sensor 35 decreases in accordance with the increase of the oxygen concentration, whereas the output value of the ammonia sensor increases in accordance with the increase of the oxygen concentration. Note that, in general, an output value of a gas sensor changes in accordance with oxygen concentration, but different reactions, such an increase of the output value, a decrease of the output value, and a change of an output curve, are made depending on sensors. Further, even in similar ethanol sensors, due to a difference of detection methods and a difference of structures, an output value may increase or decrease in a low oxygen state.

As described above, while the oxygen concentration in the laser optical path 15 changes even when the impure gases are not mixed in the laser optical path 15, the output value of each of the ethanol sensor 35 and the ammonia sensor changes, so that determination of whether or not the impure gases enter the laser optical path 15 is not performed. Accordingly, in the present embodiment, the output values of the impure gas sensors, such as the ethanol sensors 34, 35, are corrected based on the output value of the oxygen sensor 36, whereby a mixing of the impure gases in the laser optical path 15 can be detected. Note that, when ethanol is mixed in the laser optical path 15, not only the ethanol sensors but also the ammonia sensor react. The ethanol sensors react also when ammonia is mixed in the laser optical path 15. In other words, the ethanol sensors sensitively react against ethanol, but also react against an impure gas other than the ethanol.

Figure 3:
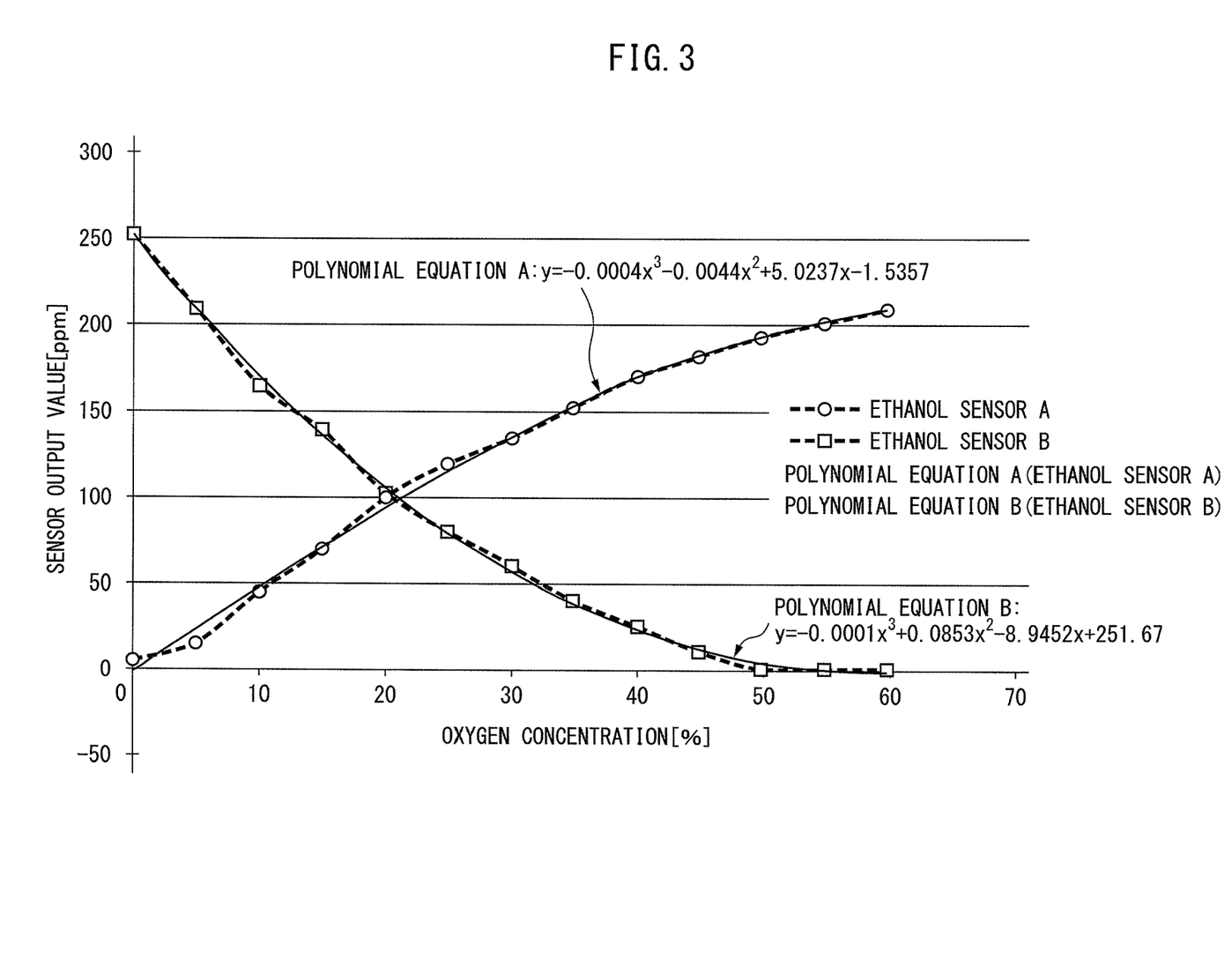
FIG. 3 is a graph illustrating a change of a sensor output value relative to oxygen concentration that is examined in advance with respect to each of two types of ethanol sensors and an approximate equation thereof.

In addition, to perform the correction as described above, how the output value of each of the ethanol sensors 34, 35 changes relative to the oxygen concentration is examined in advance to determine an approximate equation of a change of the sensor output values.

FIG. 3 is a graph illustrating a sensor output value when oxygen concentration of a gas containing 100 ppm ethanol is changed that is examined in advance with respect to each of two types of ethanol sensors A, B and an approximate equation thereof. When the above approximate equation is determined, the ethanol sensors A, B having detection methods different from each other are prepared, and the ethanol sensors A, B are installed in a chamber having the same configuration as that of the laser optical path 15 of the laser processing system as illustrated in FIG. 1. Then, as illustrated in FIG. 3, the oxygen concentration was increased while an ethanol concentration in the chamber in which the ethanol sensors A, B are housed is maintained, and each time that the oxygen concentration was increased by 5%, a sensor output value (concentration) of each of the ethanol sensors A, B was sequentially measured. At this time, it is assumed that the impure gases other than the ethanol are not mixed in the chamber in which the ethanol sensors A, B are housed as described above. Then, from results measured, an approximate equation of the sensor output value (see polynomial equations A, B as indicated in FIG. 3) with respect to each of ethanol sensors A, B was determined. Note that, as apparent from FIG. 3, even the similar ethanol sensors detecting ethanol may also greatly differ in the sensor output value when the detection methods of the sensors are different. Thus, determining the approximate equation of the sensor output value with respect to every sensor is needed.

Determining such an approximate equation in advance allows the output value of each of the ethanol sensors A, B that changes in reaction to the oxygen concentration to be estimated. Further, as described below, when a galvanic cell type oxygen sensor is adopted as the oxygen sensor 36, there is a proportional relationship between the oxygen concentration and an output value (voltage value) of the galvanic cell type oxygen sensor. Accordingly, the oxygen concentration can be obtained from the output value (voltage value) of the galvanic cell type oxygen sensor.

Then, in the laser processing system as illustrated in FIG. 1, the output value of each of the ethanol sensors 34, 35 is corrected by such a method as described below. Hereinafter, a method of correcting the output value of the ethanol sensor 34 as an exemplar will be described. First, with respect to the ethanol sensor 34, the approximate equation of the sensor output value is determined in advance. For example, the approximate equation of the sensor output value (i.e. $y=f(x)$), such as the polynomial equation A as indicated in FIG. 3, is determined in advance. Further, the output value (i.e. $y=f(x=21\%)$) of the sensor at the oxygen concentration of 21%, i.e., in the general air is stored. Then, a change of the oxygen concentration in the laser optical path 15 is monitored with reference to the output value x (concentration) of the oxygen sensor 36, while a change of the ethanol concentration is also monitored with reference to the output value Y of the ethanol sensor 34.

Further, each of the output value x of the oxygen sensor 36 and the output value Y of the ethanol sensor 34 is actually obtained with respect to every predetermined micro time, while the sensor output value of the ethanol sensor 34 that is outputted to react only to oxygen concentration change is estimated. Thus, for example, first, from the actual output value x1 of the oxygen sensor 36 that is actually obtained at a certain time t1 and the approximate equation (i.e. $y=f(x)$) of the sensor output value of the ethanol sensor 34 that is determined in advance, the estimated output value $y1(=f(x1))$ of the ethanol sensor 34 relative to the actual output value x1 of the oxygen sensor 36 at the time t1 is calculated. Moreover, when the oxygen concentration is 21% and the ethanol concentration is 100 ppm, the output value of the ethanol sensor 34 is denoted by $y_{21}$.

Then, the estimated output value y1 that is calculated is subtracted from the actual output value Y of the ethanol sensor 34 that is actually obtained at the time t1, and further the output value $y_{21}$ when the oxygen concentration is 21% and the ethanol concentration is 100 ppm is added, whereby the actual output value Y ($Y-y1+y_{21}$) of the ethanol sensor 34 is corrected. Note that the actual output value of the other ethanol sensor 35 is also corrected by the same method as that of the ethanol sensor 34 as described above.

In the present embodiment, by such a correction method as described above, the output value of each of the ethanol sensors 34, 35 that changes in accordance with the oxygen concentration in the laser optical path 15 is corrected. Then, the corrected output value of each of the ethanol sensors 34, 35 is monitored so that a mixing of ethanol in the laser optical path 15 can be accurately detected without being influenced by a change of the oxygen concentration in the laser optical path 15. In other words, the laser processing system according to the present embodiment can highly accurately detect a mixing of impure gases in a laser optical path even when such a purge gas (for example, an air in which carbon dioxide is reduced, nitrogen-rich gas, or nitrogen gas) as to change the oxygen concentration in the laser optical path is used.

Note that, as the ethanol sensors 34, 35 in the present embodiment, a catalytic combustion type ethanol sensor having such a configuration as described below is preferably adopted. For example, the catalytic combustion type ethanol sensor is made of a sensor element that reacts against ethanol which is a combustible gas and a reference element that fails to react against the ethanol. The sensor element includes a heater coil made of a noble metal, such as platinum, and a combustion catalyst layer formed on an outer circumference of the heater coil. The combustion catalyst layer is made by, for example, dispersing a combustion catalyst, such as platinum and palladium, over an alumina. On the other hand, the reference element is a combustion catalyst layer of a component constituting the sensor element that is composed only of an alumina to which the combustion catalyst is not added.

When ethanol that is a combustible gas contacts with a surface of the sensor element of the above ethanol sensor, combustion occurs due to a catalytic action of the noble metal of the combustion catalyst layer, a temperature of the heater coil increases, and an electric resistance increases. On the other hand, in the reference element, combustion does not occur even in contact with ethanol, and accordingly, the electric resistance does not change. When the ethanol sensor made of such a sensor element and a reference element is exposed to ethanol, only the electric resistance of the sensor element increases. At this time, a difference of the electric resistance between the sensor element and the reference element is measured as a voltage value using a Wheatstone bridge circuit, so that the ethanol concentration is calculated. In other words, since there is a proportional relationship between the voltage value and the ethanol concentration, the ethanol concentration can be calculated based on the measured voltage value. Thus, the laser processing system according to the present embodiment can also calculate the ethanol concentration based on the output value of the impure gas sensors (each of the ethanol sensors 34, 35). However, in the present invention, since it is sufficient that whether or not the impure gases were mixed in the laser optical path 15 as illustrated in FIG. 1 can be determined, the output value of each of the ethanol sensors 34, 35 may be only monitored and the ethanol concentration may not be calculated. Note that, in a manner similar to the impure gas sensors 34, 35 in the present embodiment, to change a concentration range of the ethanol concentration that can be measured, a composition, a surface area, and the like of the combustion catalyst layer of the sensor element as described above may be changed, and thereby an increase rate of the electric resistance and a combustion heat when ethanol contacts with the combustion catalyst layer may be changed.

Further, as the oxygen sensor 36 in the present embodiment, a galvanic cell type oxygen sensor having such a configuration as described below is preferably adopted. For example, the galvanic cell type oxygen sensor includes a cathode made of a noble metal, such as gold and platinum, an anode made of lead, and a recessed case housing the cathode and the anode, in which the cathode and the anode are connected to each other by a lead wire. Then, the recessed case is filled with an electrolytic solution, an opening portion of the case is plugged by a gas-permeable thin film, and to the thin film, the noble metal cathode closely adheres. When the oxygen in the air outside the case permeates the thin film, a reduction reaction of the oxygen occurs at the noble metal cathode inside the case and an oxidation reaction occurs at the lead anode inside the case. Along with the reactions, an electric current flowing through the lead wire is converted through a load resistance, such as a thermistor, into a voltage while a value of the voltage is measured, so that the oxygen concentration is calculated. In other words, when the oxygen concentration decreases, the reduction reaction of the oxygen at the cathode decreases, so that the voltage at both ends of the thermistor also decreases. Since there is thus a proportional relationship between the value of the voltage and the oxygen concentration, the oxygen concentration can be calculated based on the detected voltage value. Consequently, the laser processing system according to the present embodiment can also calculate the oxygen concentration based on the output value of the oxygen sensor 36. Note that, in the present embodiment, when the output value of each of the ethanol sensors 34, 35 is corrected, the output value of the oxygen sensor 36 may be merely obtained. In other words, a corresponding relationship between the output value of the oxygen sensor 36 and the output value of each of the ethanol sensors 34, 35 is examined in advance, an approximate equation, a table, and the like of the corresponding relationship are prepared and stored in the numerical value calculator 37, so that the oxygen concentration may not be calculated.

Figure 4:
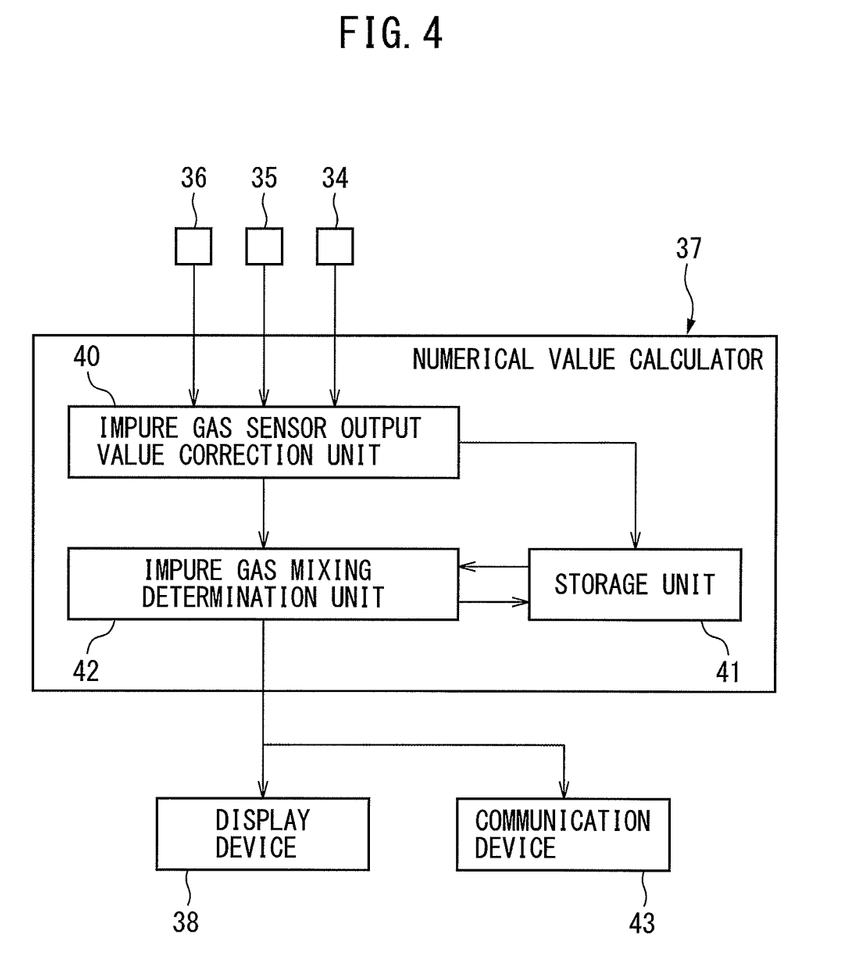
FIG. 4 is a block diagram illustrating a configuration of a numerical value calculator according to the first embodiment.

Next, a configuration of the numerical value calculator 37 will be described.

FIG. 4 is a block diagram illustrating a configuration example of the numerical value calculator 37.

As illustrated in FIG. 4, the numerical value calculator 37 includes an impure gas sensor output value correction unit 40, a storage unit 41, and an impure gas mixing determination unit 42.

The impure gas sensor output value correction unit 40 monitors the output value of the oxygen sensor 36 and corrects the output value of each of the ethanol sensors 34, 35 that changes in accordance with the oxygen concentration in the laser optical path 15. The correction method has been described above. Further, the storage unit 41 stores a determination threshold value set in advance with respect to each of the ethanol sensors 34, 35. The impure gas mixing determination unit 42 compares the output value of the ethanol sensor 34 that is corrected by the impure gas sensor output value correction unit 40 and the determination threshold value set in advance with respect to the ethanol sensor 34, and determines based on a comparison result thereof whether or not ethanol was mixed in the laser optical path 15. Similarly, the impure gas mixing determination unit 42 compares the output value of the ethanol sensor 35 that is corrected by the impure gas sensor output value correction unit 40 and the determination threshold value set in advance with respect to the ethanol sensor 35, and determines based on a comparison result thereof whether or not ethanol was mixed in the laser optical path 15. The determination threshold values are thus used so that, without accurately detecting a type and concentration of the impure gases, whether or not the impure gases were mixed in the laser optical path 15 can be determined. Accordingly, the impure gas mixing determination unit 42 has a low-cost and simple configuration.

Note that, as described above, as the ethanol sensors 34, 35, gas sensors having detection concentrations different from each other are used. Further, the ethanol sensor 34 on one hand is a gas sensor that detects an ethanol having a lower concentration than the ethanol sensor 35 on the other hand, in other words, a gas sensor having a higher sensitivity than the ethanol sensor 35 on the other hand. Consequently, when the output value of the ethanol sensor 34 changes in accordance with a change of the oxygen concentration, the output value may exceed a maximum value, which causes saturation, and may be no longer capable of detecting ethanol. In contrast, the ethanol sensor 35 on the other hand is a gas sensor having a lower sensitivity than the ethanol sensor 34 on one hand. Consequently, even when the output value of the ethanol sensor 35 changes in accordance with a change of the oxygen concentration, the output value has a sufficient allowance for the maximum value so that ethanol can be detected. In other words, even when the output value of the impure gas sensor having a lower detection concentration, i.e., having a higher sensitivity exceeds the maximum value and saturation occurs, the impure gases can be detected using the impure gas sensor having a higher detection concentration, i.e., having a lower sensitivity. As thus described, in the present invention, at least the two impure gas sensors (the ethanol sensors 34, 35) having different detection concentrations are desirably installed in the laser optical path 15.

Further, to the numerical value calculator 37, the display device 38 that displays a determination result of the impure gas mixing determination unit 42 is preferably connected. Moreover, the display device 38 may preferably display, together with the determination result of the impure gas mixing determination unit 42, a change of the output value of each of the ethanol sensors 34, 35 and the oxygen sensor 36 with passage of time and the output value of each of the ethanol sensors 34, 35 that is corrected by the impure gas sensor output value correction unit 40 with passage of time through classification by respective colors. Accordingly, a mixing timing of the impure gases becomes clear and specifying a cause of the mixing of the impure gases is facilitated.

Further, as illustrated in FIG. 4, the numerical value calculator 37 preferably includes a communication device 43 that communicates the determination result of the impure gas mixing determination unit 42 to the exterior of the laser processing system. The communication device 43 preferably communicates, by, for example, sound, light, or a combination thereof, that the impure gases that influence the propagation of the laser beam 11 was mixed in the laser optical path 15. Thereby, an operator of the laser processing system 10 can promptly recognize a mixing of the impure gases in the laser optical path 15. Further, a malfunction during laser processing can be prevented beforehand or laser processing can be stopped at an early stage so that damage due to a processing defect can be restrained to a minimum. In addition, a cause of a malfunction during laser processing can be promptly specified and eliminated so that productivity is also improved.

Further, the storage unit 41 of the numerical value calculator 37 preferably stores, at every certain time, the output value of each of the ethanol sensors 34, 35 and the oxygen sensor 36 together with the date and hour at which the output value is outputted. In other words, a cause of a mixing of the impure gases in the laser optical path 15 is often a malfunction of the laser processing system 10 itself, such as a sealing degree of the laser optical path 15. If the storage unit 41 stores, at every certain time, the output values of the impure gas sensors together with the date and hour at which the output values are outputted, when abnormality is generated, a cause of the abnormality can be easily specified using information thus stored.

Figure 5:
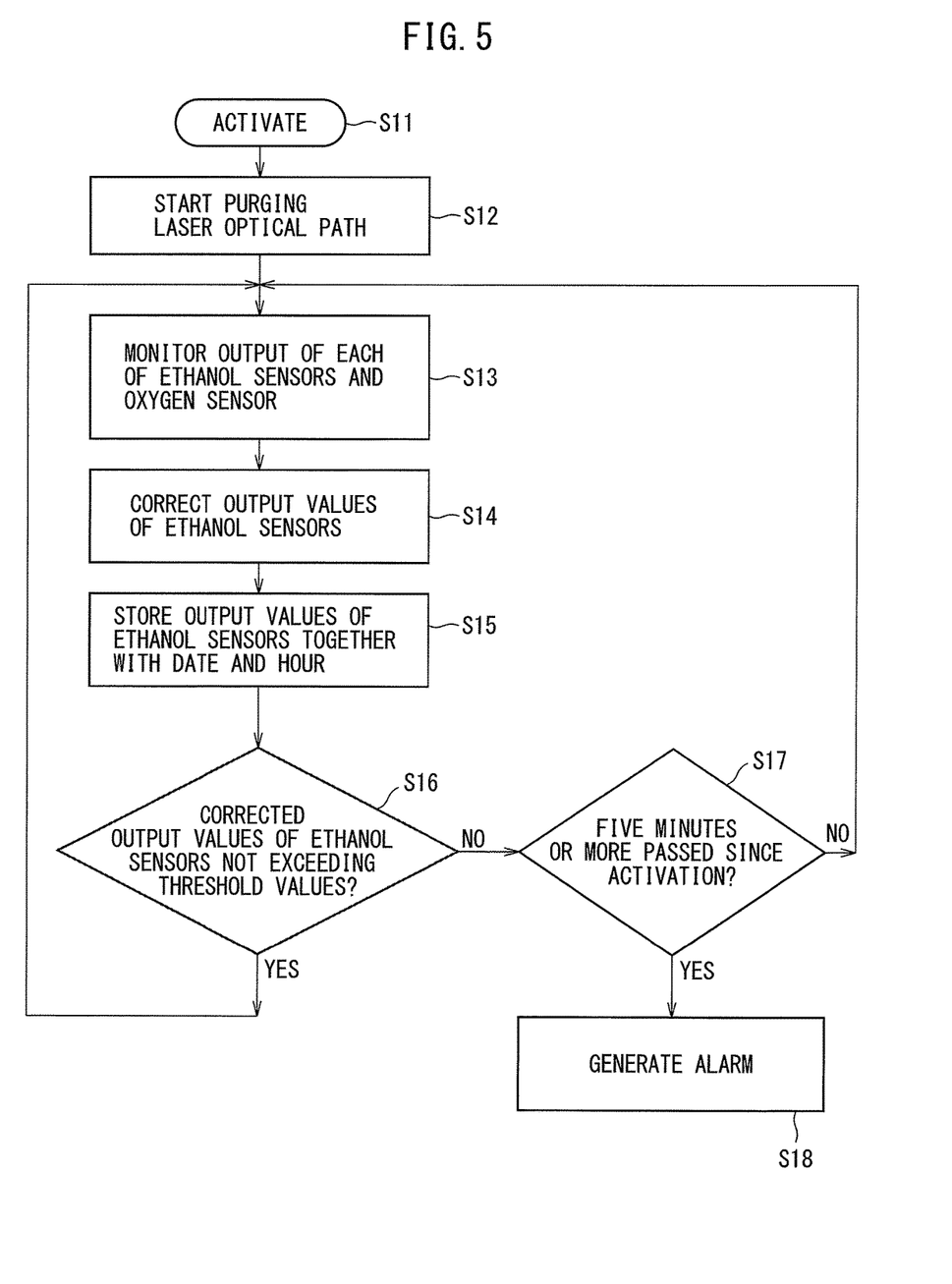
FIG. 5 is a flowchart illustrating an example of an operation of the laser processing system according to the first embodiment.

Next, an example of an operation of the laser processing system 10 as described above will be described with reference to FIGS. 1, 4, and 5. FIG. 5 is a flowchart illustrating an example of an operation of the laser processing system 10 according to the first embodiment.

First, the laser processing system 10 is activated (step S11 of FIG. 5), and purging the laser optical path 15 is started (step S12 of FIG. 5). At this time, one of the three opening and closing valves 23 illustrated in FIG. 1 is opened, and thereby the purge gas supplied in the laser optical path 15 is selected.

The numerical value calculator 37 monitors the output value of each of the ethanol sensors 34, 35 while monitoring the output value of the oxygen sensor 36 (step S13 of FIG. 5).

Subsequently, the impure gas sensor output value correction unit 40 of the numerical value calculator 37 monitors the output value of the oxygen sensor 36 and corrects the output value of each of the ethanol sensors 34, 35 that changes in accordance with the oxygen concentration in the laser optical path 15 (step S14 of FIG. 5). Further, the numerical value calculator 37 allows the storage unit 41 to store the output value of each of the ethanol sensors 34, 35 and the oxygen sensor 36 together with the date and hour at which the output value is outputted (step S15 of FIG. 5).

Then, the impure gas mixing determination unit 42 of the numerical value calculator 37 compares, respectively, the output values of the ethanol sensors 34, 35 that are corrected by the impure gas sensor output value correction unit 40 and the determination threshold values that are set with respect to the ethanol sensors 34, 35. In other words, whether or not the corrected output values of the ethanol sensors 34, 35 exceeds the respective threshold values is determined (step S16 of FIG. 5).

In step S16 as described above, when the corrected output values of the ethanol sensors 34, 35 exceeds the respective determination threshold values, proceeding to step S17 is made. In step S17, whether or not five minutes or more have passes since the laser processing system 10 is activated is determined. As a result, when five minutes or less have passed since the laser processing system 10 is activated, the ethanol sensors 34, 35 and the oxygen sensor 36 are possibly still unstable and consequently steps S13 to S15 are performed again. On the other hand, when five minutes or more have passed since the laser processing system 10 is activated, the impure gas mixing determination unit 42 determines that there is abnormality in the atmosphere in the laser optical path 15, and allows the communication device 43 to generate an alarm, such as an alarm sound (step S18 of FIG. 5).

Further, after step S16 as described above, while the laser processing system 10 is operated, processing of steps S13 to S15 is repeated, and a gas environment in the laser optical path 15 is constantly confirmed.

Second Embodiment

Next, a second embodiment of the present invention will be described. Note that, hereinafter, points different from the first embodiment as described above will be mainly described, and the same constituting elements as those in the first embodiment as described above will be assigned the same reference signs and the description thereof will be accordingly omitted.

Figure 6:
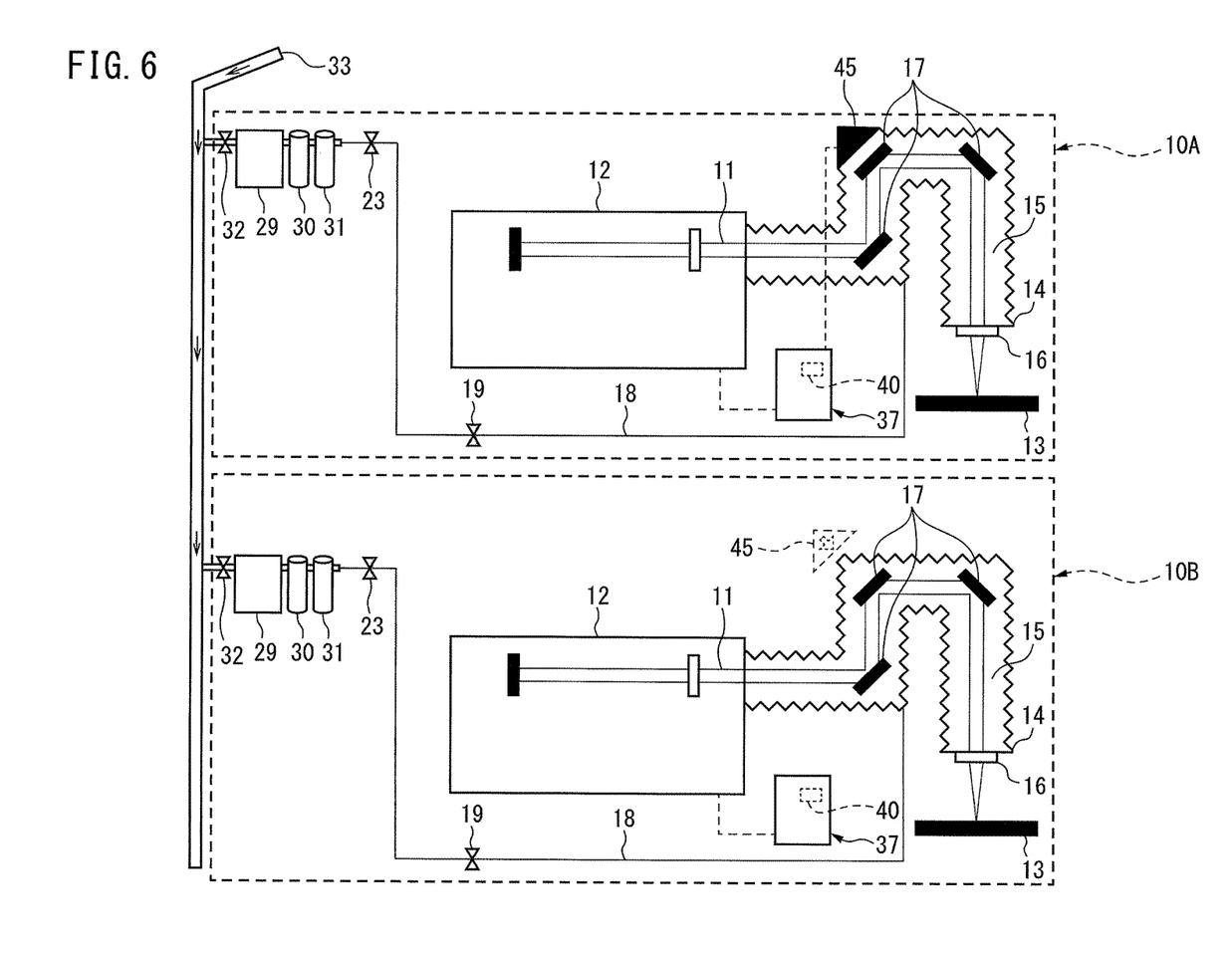
FIG. 6 is a block diagram schematically illustrating configurations of laser processing systems according to a second embodiment.

FIG. 6 is a block diagram schematically illustrating configurations of laser processing systems according to the second embodiment. As illustrated in the drawing, two laser processing systems 10A, 10B may be installed in a factory. The laser processing system 10A on one hand is an apparatus for cutting a sheet metal using a carbonic acid gas laser. The laser processing system 10B on the other hand is a system in which no impure gas sensor is installed in the laser optical path 15.

In the laser optical path 15 of the laser processing system 10A on one hand, a detachable sensor unit 45 that detects two types or more of impure gases is installed. In the sensor unit 45, an ethanol sensor, an ammonia sensor, a fluorosensor, a zirconia type oxygen sensor, and an infrared carbon dioxide concentration sensor are fixed. Further, the various gas sensors in the sensor unit 45 are connected to the numerical value calculator 37. In a point in which such a sensor unit 45 is included, the laser processing system 10A according to the second embodiment differs from the laser processing system 10 according to the first embodiment.

Moreover, in the second embodiment, as illustrated in FIG. 6, the detachable sensor unit 45 as described above can be attached to the laser processing system 10B on the other hand. In other words, when a processing defect is produced in the laser processing system 10B on the other hand, the sensor unit 45 can be detached from the laser processing system 10A on one hand and can be attached to the laser processing system 10B on the other hand. Thereby, to the laser processing system 10B on the other hand, a function of monitoring components of the purge gas in the laser optical path 15 can be added. In addition, since the impure gas sensor for detecting the impure gases that influence the propagation of the laser beam does not need to be provided to each of the plurality of laser processing systems 10A, 10B, facility costs for the whole factory can be reduced.

Note that, in FIG. 6, the two laser processing systems 10A, 10B are illustrated, but the number of the laser processing systems is not limited to two.

Third Embodiment

Next, a third embodiment of the present invention will be described. Note that, hereinafter, points different from the first embodiment and the second embodiment as described above will be mainly described, and the same constituting elements as those in the first embodiment and the second embodiment as described above will be assigned the same reference signs and the description thereof will be accordingly omitted.

Figure 7:
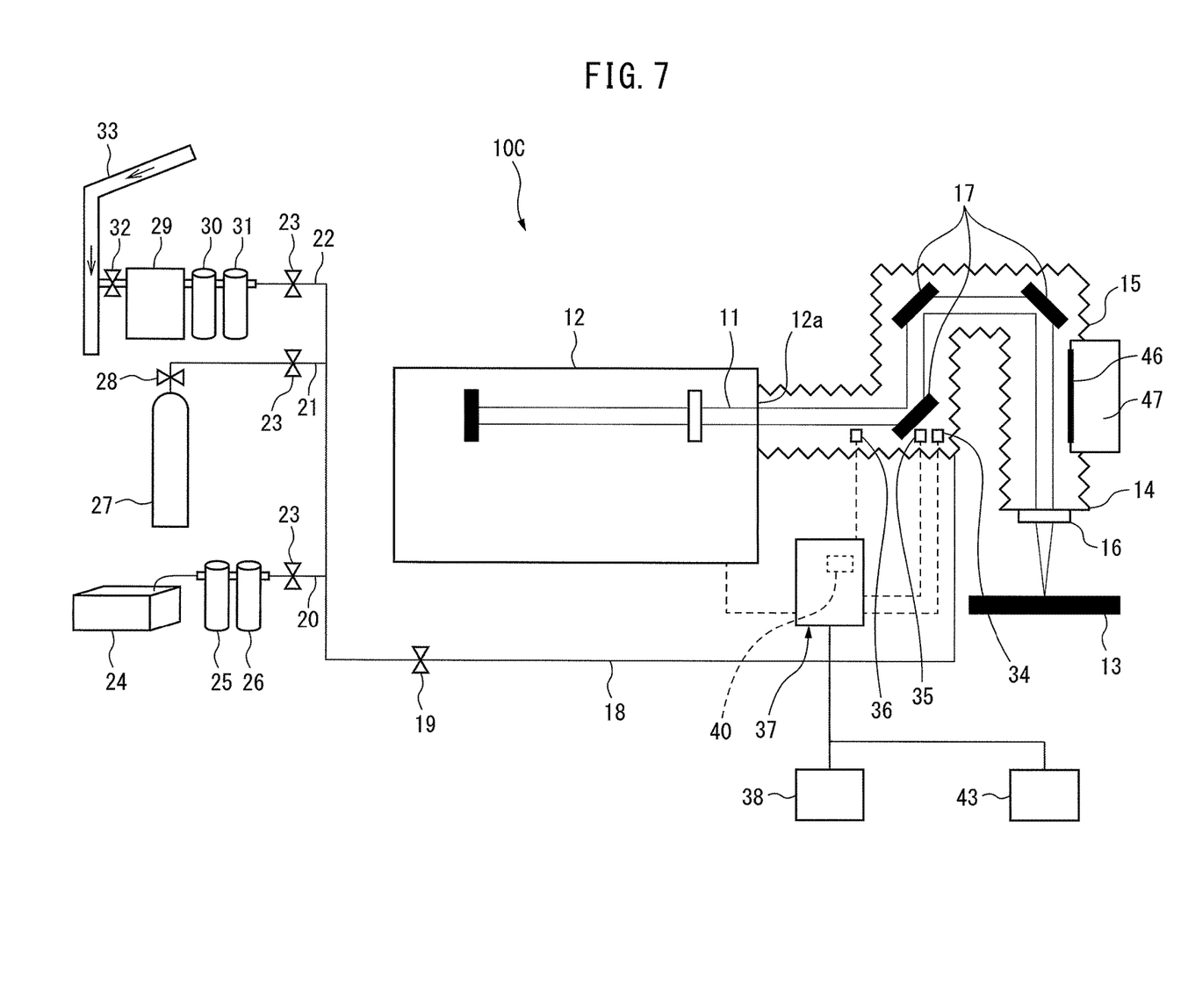
FIG. 7 is a block diagram schematically illustrating a configuration of a laser processing system according to a third embodiment.

FIG. 7 is a block diagram schematically illustrating a configuration of a laser processing system according to the third embodiment.

In contrast to the laser processing system 10 according to the first embodiment, a laser processing system 10C according to the third embodiment includes an exposure function part for exposing an impure gas adsorbent 47 that adsorbs the impure gases in the laser optical path 15. Specifically, as illustrated in FIG. 7, a shutter 46 as the exposure function part is configured at a wall portion that is a part of the laser optical path 15. Further, the shutter 46 is provided between the laser optical path 15 and the impure gas adsorbent 47. In addition, when the inside of the laser optical path 15 is opened through the shutter 46, the impure gas adsorbent 47 is exposed in the laser optical path 15. Further, in the present embodiment, a drive device (unillustrated) that drives opening and closing of the shutter 46 is preferably provided.

Note that the other configuration is the same as that of the laser processing system 10 according to the first embodiment.

Next, effects of a point of including the function of exposing the impure gas adsorbent 47 in the laser optical path 15 will be described.

For example, when gases including ammonia that causes dispersion of a carbonic acid gas laser are mixed in the laser optical path 15, decreasing ammonia concentration in the laser optical path 15 to such a concentration as to enable the laser processing takes time even by supplying the purge gas, such as nitrogen gas, into the laser optical path 15. In this case, when the purge gas, such as nitrogen gas, is supplied into the laser optical path 15 while the impure gas adsorbent 47 is exposed in the laser optical path 15, the ammonia concentration in the laser optical path 15 can be decreased in a short time. This point can be further understood from FIG. 8.

Figure 8:
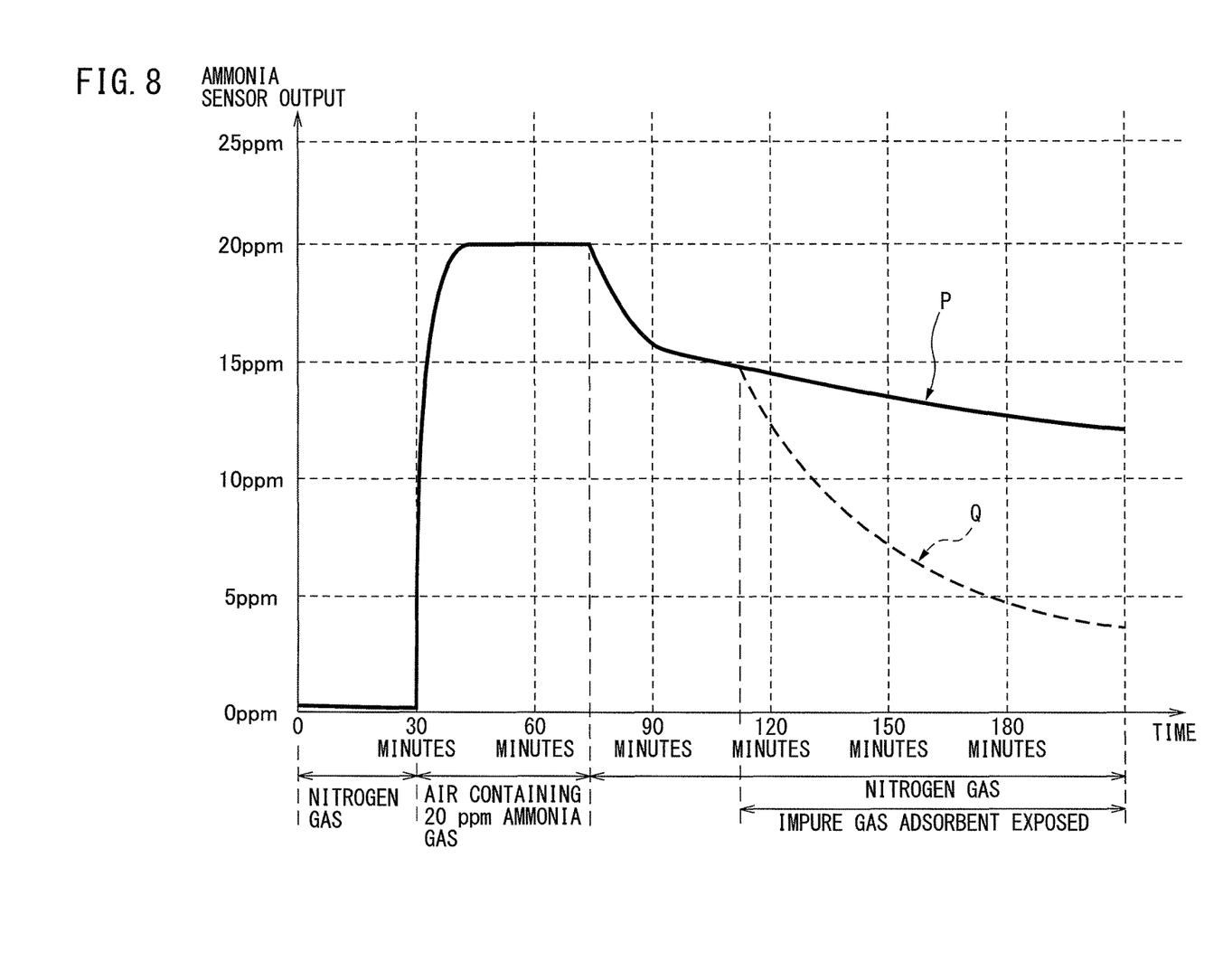
FIG. 8 is a graph illustrating effects of a function of exposing an impure gas adsorbent in the laser optical path according to the third embodiment.

FIG. 8 is a graph illustrating effects of the function of exposing the impure gas adsorbent 47 in the laser optical path 15. In particular, the graph as illustrated in FIG. 8 is obtained by the following process. First, in the laser processing system 10C as illustrated in FIG. 7, an ammonia sensor (unillustrated) is installed in the laser optical path 15 and nitrogen gas is supplied into the laser optical path 15 for approximately 30 minutes. Then, an air containing 20 ppm ammonia gas is supplied into the laser optical path 15 for approximately 45 minutes. Subsequently, the nitrogen gas is again supplied into the laser optical path 15. In other words, FIG. 8 is a graph in which a change of the ammonia concentration with passage of time while the gases supplied into the laser optical path 15 are thus sequentially switched is measured by the ammonia sensor.

As apparent from a solid line P in FIG. 8, while the nitrogen gas that replaces the air containing 20 ppm ammonia gas is supplied into the laser optical path 15, the ammonia concentration decreases in accordance with time, but a decreasing speed of the ammonia concentration is relatively slow. It is assumed that this is because a pseudo-chemical bond between a wall surface in the laser optical path 15 and ammonia is generated. When such a pseudo-chemical bond is generated, continuing supplying the nitrogen gas into the laser optical path 15 for a long time and decreasing the ammonia concentration in the laser optical path 15 to concentration at which the stable laser processing can be performed are needed. However, when the nitrogen gas that replaces the air containing the ammonia gas is supplied into the laser optical path 15 and further the impure gas adsorbent 47 is exposed in the laser optical path 15, the decreasing speed of the ammonia concentration largely increases, as indicated by a dashed line Q in FIG. 8.

Thus, in the third embodiment, when the impure gas mixing determination unit 42 as illustrated in FIG. 4 determines that the impure gases are mixed in the laser optical path 15, first, a cause of a mixing of the impure gases is eliminated. Then, it is configured that the purge gas, such as nitrogen gas, is supplied into the laser optical path 15 while the shutter 46 is opened such that the impure gas adsorbent 47 is exposed in the laser optical path 15. Thereby, as illustrated in FIG. 8, the concentrations of the impure gases in the laser optical path 15 can be decreased in a short time.

Note that typical embodiments have been described above, but the present invention is not limited to the embodiments as described above, and the embodiments as described above may be modified in various forms, structures, materials, and the like without departing from the spirit of the present invention.

EFFECTS OF INVENTION

According to the first aspect, the ninth aspect, and the tenth aspect of the present invention, the output values of the impure gas sensors that change in accordance with the oxygen concentration in the laser optical path can be corrected. Accordingly, even when such a purge gas, as to change the oxygen concentration in the laser optical path, for example, an air in which carbon dioxide is reduced, nitrogen-rich gas, or nitrogen gas, is used, a mixing of the impure gases in the laser light path can be highly accurately detected.

According to the second aspect of the present invention, even when the output value of one of the impure gas sensors which has a lower detection concentration, i.e. a higher sensitivity exceeds a maximum value and saturation occurs, the other impure gas sensor having a higher detection concentration, i.e. a lower sensitivity can be used to detect the impure gases.

According to the third aspect of the present invention, the at least two impure gas sensors that detect different gas types are provided so that the various types of impure gases that influence propagation of the laser beam can be monitored.

According to the fourth aspect of the present invention, the determination threshold value that is stored in advance is used so that, without accurately detecting a type and concentration of the impure gases, whether or not the impure gases were mixed in the laser optical path can be determined. Accordingly, the impure gas mixing determination unit has a low-cost and simple configuration.

According to the fifth aspect of the present invention, the communication device communicates a mixing of the impure gases in the laser optical path so that an operator of the laser processing system can promptly recognize the mixing of the impure gases in the laser optical path. Accordingly, a malfunction during laser processing can be prevented beforehand, laser processing can be stopped at an early stage, or an alarm can be generated to stop the laser processing system so that damage due to a processing defect can be restrained to a minimum. In addition, a cause of a malfunction during laser processing can be promptly specified and eliminated so that productivity is also improved According to the sixth aspect of the present invention, when a mixing of the impure gases in the laser optical path is determined, the exposure function part exposes the impure gas adsorbent in the laser optical path so that concentrations of the impure gases in the laser optical path can be decreased in a short time.

According to the seventh aspect of the present invention, the storage unit stores the output value of each of the impure gas sensors and the oxygen sensor when laser processing is performed together with date and hour at which the output value is outputted. Accordingly, when a malfunction of laser processing occurs, an operator of the laser processing system can easily specify a cause of the malfunction using such stored information.

According to the eighth aspect of the present invention, the detachable sensor unit including the oxygen sensor and the at least one impure gas sensor is provided in the laser optical path. Accordingly, the sensor unit is attached to the other laser processing system failing to include the impure gas sensors and thereby a mixing of the impure gases in the laser optical path in the other laser processing system can be monitored.

The invention claimed is:

1. A laser processing system comprising:
 a laser oscillator configured to oscillate a laser beam;
 a laser optical path that guides the laser beam from the laser oscillator to an object to be processed;
 an oxygen sensor for detecting oxygen and one or more impure gas sensors for detecting an impure gas influencing propagation of the laser beam that are installed in the laser optical path;
 an impure gas sensor output value correction unit that is configured to correct an output value of the impure gas sensor based on an output value of the oxygen sensor; and
 an impure gas mixing determination unit that is configured to determine whether or not the impure gas was mixed in the laser optical path, based on a comparison between the output value of the impure gas sensor that is corrected by the impure gas sensor output value correction unit and a determination threshold value that is stored in advance.

2. The laser processing system according to claim 1, comprising at least two impure gas sensors that have different detection concentrations.

3. The laser processing system according to claim 1, comprising at least two impure gas sensors that detect different gas types.

4. The laser processing system according to claim 1, further comprising a communication device that is configured to communicate a mixing of the impure gas when the impure gas mixing determination unit determines that the impure gas was mixed in the laser optical path.

5. The laser processing system according to claim 1, further comprising:
 an impure gas adsorbent that adsorbs the impure gas; and
 an exposure function part that is configured to expose the impure gas adsorbent in the laser optical path when the impure gas mixing determination unit determines that the impure gas was mixed in the laser optical path.

6. The laser processing system according to claim 1, further comprising a storage unit that stores the output value of each of the impure gas sensor and the oxygen sensor together with date and hour at which the output value is outputted.

7. The laser processing system according to claim 1, wherein
 the laser optical path is provided with a detachable sensor unit, and
 the sensor unit includes the oxygen sensor and at least one of the impure gas sensors.

8. The laser processing system according to claim 1, comprising a purge gas supply line for supplying a purge gas into the laser optical path, wherein the purge gas is air that is supplied into the laser optical path through a high polymer filter, an activated carbon filter, a hollow fiber filter, or an oil mist filter.

9. The laser processing system according to claim 1, wherein the oxygen sensor or the impure gas sensor is a controlled potential electrolysis type gas sensor, a galvanic cell type gas sensor, a catalytic combustion type gas sensor, a gas heat conduction type gas sensor, a zirconia type gas sensor, a polaro type gas sensor, or a semiconductor type gas sensor.

10. A laser processing system comprising:
 a laser oscillator configured to oscillate a laser beam;
 a laser optical path that guides the laser beam from the laser oscillator to an object to be processed;
 an oxygen sensor for detecting oxygen and at least two impure gas sensors for detecting different gas types of impure gases influencing propagation of the laser beam that are installed in the laser optical path; and
 an impure gas sensor output value correction unit that is configured to correct an output value of the impure gas sensor based on an output value of the oxygen sensor.

11. A laser processing system comprising:
 a laser oscillator configured to oscillate a laser beam;

a laser optical path that guides the laser beam from the laser oscillator to an object to be processed;

an oxygen sensor for detecting oxygen and one or more impure gas sensors for detecting an impure gas influencing propagation of the laser beam that are installed in the laser optical path; and an impure gas sensor output value correction unit that is configured to correct an output value of the impure gas sensor based on an output value of the oxygen sensor; wherein the laser optical path is provided with a detachable sensor unit, and the sensor unit includes the oxygen sensor and at least one of the impure gas sensors.

12. A laser processing system comprising:

a laser oscillator configured to oscillate a laser beam;

a laser optical path that guides the laser beam from the laser oscillator to an object to be processed;

an oxygen sensor for detecting oxygen and an impure gas sensor for detecting an impure gas influencing propagation of the laser beam that are installed in the laser optical path;

an impure gas sensor output value correction unit that is configured to correct an output value of the impure gas sensor based on an output value of the oxygen sensor; and a purge gas supply line for supplying a purge gas into the laser optical path; wherein the purge gas is air that is supplied into the laser optical path through a high polymer filter, an activated carbon filter, a hollow fiber filter, or an oil mist filter.

* * * * *